(12) United States Patent
Coelho Do Sameiro Espregueira Mendes

(10) Patent No.: US 9,451,918 B2
(45) Date of Patent: Sep. 27, 2016

(54) DEVICE FOR MEASURING KNEE LAXITY

(75) Inventor: Joao Coelho Do Sameiro Espregueira Mendes, Oporto (PT)

(73) Assignee: FJR, SGPS, S.A., Oporto (PT)

( * ) Notice: Subject to any disclaimer, the term of this patent is extended or adjusted under 35 U.S.C. 154(b) by 622 days.

(21) Appl. No.: 13/702,058

(22) PCT Filed: Dec. 10, 2010

(86) PCT No.: PCT/PT2010/000065
§ 371 (c)(1),
(2), (4) Date: Jan. 31, 2013

(87) PCT Pub. No.: WO2011/152746
PCT Pub. Date: Dec. 8, 2011

(65) Prior Publication Data
US 2013/0204119 A1 Aug. 8, 2013

(30) Foreign Application Priority Data

Jun. 4, 2010 (PT) .................................. 105144

(51) Int. Cl.
*A61B 5/00* (2006.01)
*A61B 5/103* (2006.01)
*A61B 5/11* (2006.01)
(Continued)

(52) U.S. Cl.
CPC ............ *A61B 5/4585* (2013.01); *A61B 5/055* (2013.01); *A61B 5/103* (2013.01); *A61B 5/1107* (2013.01); *A61B 5/1121* (2013.01);
(Continued)

(58) Field of Classification Search
CPC A61B 5/4528; A61B 5/4533; A61B 5/6828; A61B 5/1121

USPC .................................................. 600/587, 595
See application file for complete search history.

(56) References Cited

U.S. PATENT DOCUMENTS 3,521,876 A * 7/1970 Smith .................. A61B 6/0421
 248/509
4,323,080 A * 4/1982 Melhart ................. A61B 6/505
 128/882
(Continued)

FOREIGN PATENT DOCUMENTS

DE 3925014 1/1991
FR 2906706 4/2008

OTHER PUBLICATIONS

English machine translation of DE3925014 from European Patent Office Website. Acquired on Apr. 20, 2015.*
PCT/PT2010/000065, International Search Report, Apr. 5, 2011.

*Primary Examiner* — Adam J Eiseman
(74) *Attorney, Agent, or Firm* — Lucas & Mercanti, LLP

(57) ABSTRACT

The present invention relates to a device (1) for measuring the knee laxity, with or without use of additional means of diagnosis such as computed axial tomography and magnetic resonance imaging, evaluating the instability of the knee due to rupture of any ligament, namely the anterior cruciate ligament, posterior cruciate ligament, postero-internal capsule, postero-external capsule, as well as around the axis of an orthonormal referential, that comprises three parts respectively to accept and retain the thigh, leg and foot.
The device (1) includes independent means (20) and (21) to push backward the anterior zone of the leg and to push forward the posterior zone of the leg, and independent means (12) and (13) to push the part (5) for support and fixation of the foot in clockwise direction and in anticlockwise direction.

12 Claims, 3 Drawing Sheets

(51) Int. Cl.
*A61B 5/055* (2006.01)
*A61B 6/03* (2006.01)

(52) U.S. Cl.
CPC .............. *A61B 5/4528* (2013.01); *A61B 5/70* (2013.01); *A61B 6/03* (2013.01); *A61B 5/6812* (2013.01); *A61B 5/6828* (2013.01); *A61B 5/6829* (2013.01); *A61B 2503/10* (2013.01); *A61B 2505/05* (2013.01)

(56) References Cited

U.S. PATENT DOCUMENTS 5,267,949 A * 12/1993 De La Torre ......... A61F 5/3761
                                                                    128/882
5,349,956 A     9/1994 Bonutti
6,499,484 B1  12/2002 Salminen
8,226,590 B2 * 7/2012 Tucker ..................... A61B 6/04
                                                                    128/845

* cited by examiner

DEVICE FOR MEASURING KNEE LAXITY

FIELD OF THE INVENTION

The present invention relates to a device for evaluating the instability of the knee due to rupture of any ligament, namely the anterior cruciate ligament, posterior cruciate ligament, postero-internal capsule, postero-external capsule, as well as in all the axis of orthonormal, anterior, posterior, antero-internal, antero-external, postero-internal and postero-external referentials.

In recent decades, the number of injuries in lower limb joints has significantly increased. This problem affects both athletes and any other individuals who may be victims of accidents and/or congenital diseases.

This type of injuries and traumas leads to an individual inability since it creates instability of the knee, preventing their normal functions (rotation, impulse and extension) thus creating an incapacity for the individual to execute his daily tasks.

In fact, the treatment of the knee ligaments ruptures varies depending on the severity and can involve different therapies, ranging from physiotherapy to surgery.

However, in order to apply the appropriate treatment, it is essential to perform an accurate and precise diagnosis of the injury type.

Nowadays, the injury diagnosis is achieved through an inquiry presented to the patient (where and how the incident occurred, what type of activity was being executed and how often), analysis of the injured area and visualization of the injury through clinical examination using various diagnostic methods.

However, these diagnostic tests, which may include radiographs (x-rays), computed axial tomography scan (CAT-scan), magnetic resonance imaging (MRI) and arthroscopy (injured joint observation through insertion of a small instrument into the joint), can't accurately measure the severity of the injury.

The present invention allows an accurate assessment of the laxity, not only for the anterior and posterior cruciate ligaments but for all the others knee ligaments.

The device for measuring the knee laxity is not just intended to overcome all the drawbacks with state-of-art devices, but it represents a new concept and a major scientific and technical improvement in measuring the knee laxity (anterior—posterior and rotations) and in subsequent treatment.

By making these measurements, it will be possible to define exactly who are the patients, that because of the ligaments rupture, will need surgery and those which only require preservation treatment.

TECHNICAL BACKGROUND

Devices KT1000 and KT2000 sold by MEDmetric® Corporation are known in the market and they roughly measure the anterior and posterior tibial translation, which is measured from the outside of the leg and has the muscle mass and the soft tissues (more or less compressible and variable from individual to individual) as an error factor, being this measurement taken only in mm.

Ferromagnetic materials are used in these devices, what makes them unusable inside MRI or CAT-scan devices is they interfere with the image processing. These devices are used only for evaluation of the anterior cruciate ligament rupture and posterior cruciate ligament rupture.

EP 1 125 567 discloses a device allowing an accurate measuring of the tibial anterior translation and internal rotation because it can be used inside MRI or CAT-scan devices, not interfering with image processing since it doesn't include ferromagnetic materials.

The measurements are made in the MRI or CAT-scan images, between two bone structures (femur and tibia) which grants them great accuracy. These measurements can be related to the associated injuries observed in the images (meniscus, cartilage, etc.).

This device disclosed in patent EP 1 125 567 is only used in the ruptures of the anterior cruciate ligament. On account of this uniqueness, it doesn't allow an accurate diagnosis of associate instabilities.

On account of those limitations, the device disclosed in patent EP 1 125 567 does not allow distinction of those patients who need a surgical technique with greater or lesser rotation control, and also does not allow the evaluation of patients with associate ligament injuries (most common).

The device described in this invention allows an accurate measuring of the tibial anterior translation and tibial posterior translation, the internal rotation and external rotation because it can be used inside devices of MRI or CAT-scan, not interfering with image processing since it doesn't include ferromagnetic materials.

The device for measuring the knee laxity described in the invention includes materials suitable for use in MRI or CAT-scan for instance, inter alia, composites, plastics, resins and carbon fibers.

With the assistance of the device described in this invention, the measurements are made in the images from MRI and CAT-scan between two bone structures, femur and tibia.

These measurements can be related to associated injuries observed in the images, like inter alia, with meniscus, cartilages, etc.

The device for measuring the knee laxity described in the present invention has the ability to measure the knee rotation without using images from MRI and CAT-scan.

The device is used for ruptures of the anterior cruciate ligament and posterior cruciate ligament, antero-external, postero-external, antero-internal and postero-internal instabilities, instabilities in all directions, and also to evaluate all possible rotational instabilities of the knee.

It is therefore possible to obtain accurate diagnoses and subsequent modifications of the surgical indications, allowing the separation of those patients who need surgery from those who just need physiotherapy.

This device is quite innovative and will radically change the orthopedics market since:

Until now, with prior art technique, the instability measurement is made roughly and by approximation, while with this new device it will be possible to measure the knee instability with accuracy.

Until now, the treatment and surgeries for knee traumatic injury were generic, but with this new device it will be possible to get and set a real diagnosis, leading to more appropriate treatments which means one can decide whether or not to perform surgery with greater precision, and can choose between different types of surgery depending on the needs, leading to a higher success rate in patients' recovery.

SUMMARY OF THE INVENTION

The device of the present invention for measuring the knee laxity is a medical or surgical equipment for measuring accurately and directly the abnormal movement of the injured knee joint, and can be used inside the CAT-scan and MRI devices.

This device for measuring the knee laxity, with or without use of additional means of diagnosis as CAT-scan and MRI, evaluates knee instability caused by rupture of any ligament, namely the anterior cruciate ligament, posterior cruciate ligament, postero-internal capsule, postero-external capsule, as well as around axis orthonormal, anterior, posterior, antero-internal, antero-external, postero-internal and postero-external referential. Essentially it comprises a part to receive and hold the thigh with belts, a part to receive and hold the leg and a part to receive and hold the foot with belts.

The present invention comprises independent means to push the anterior zone of the leg backward and to push the posterior zone of the leg forward, and the means to push the foot to the left and right sides.

The device also includes a part for posterior support and fixation of the foot, allowing it to alternatively rotate to the left or to the right according to the force exerted on the part for posterior support and fixation of the foot, around a shaft that runs through the said part for posterior support and fixation of the foot and through a supporting part which is articulated.

The present invention can be placed inside a MRI or CAT-scan device to help measuring the laxity of a knee with ligament rupture, in order to obtain one or more images of antero-posterior translation.

Therefore, a rotation will be executed, which may be measured between two bony points on the tibia and femur with high precision, the measurement being performed on the image without distortion since the materials used will be tested in order not to interfere with the image.

Additionally, the device object of this invention will allow measuring the rotation between femur and tibia caused by ligament ruptures, the most serious knee injuries, which is the most important cause of instability and knee failure.

By measuring the rotation between tibia and femur inside the MRI and CAT-scan device, one can select exactly who are the patients which need surgery and those which only require physiotherapy treatment.

Since the device object of the present invention can be used in an of MRI or CAT-scan environment, all associated injuries, occurring for instance and inter alia with the menisci, cartilage, etc., can be correlated with an injury severity that can be quantified.

BRIEF DESCRIPTION OF THE DRAWINGS

The following description is made with reference to the accompanying drawings which are presented just as a non-limiting example, in which.

Figure 1:
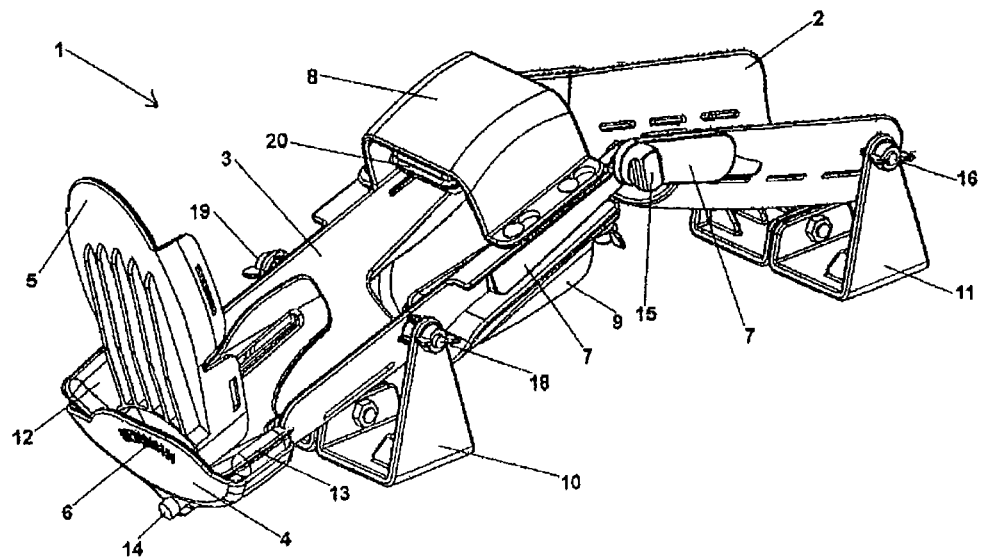
FIGS. 1 and 2 are perspective views of the device described in the present invention.

LEGEND OF THE FIGURES device (1) for measuring the knee laxity
part (2) for posterior support and fixation of the thigh
part (3) for posterior support and fixation, of the leg
supporting piece (4)
part (5) for posterior support and fixation of the foot
scale (6) placed in the part (5) for posterior support and fixation of the foot
articulation elements (7)
removable part (8) for front fixation of the thigh
removable part (9) for posterior fixation of the thigh
moving part (10) with flat base
moving part (11) with flat base
means (12) to push the foot in clockwise direction
means (13) to push the foot in anticlockwise direction
shaft (14)
tightening nuts (15) for the articulation elements
tightening nuts (16, 19) for the moving parts (10, 11)
means (20) to push the leg backwards
means (21) to push the leg forward

DETAILED DESCRIPTION OF THE INVENTION

As can be seen in FIGS. 1, 2, 3 and 4, the device (1) described in this invention is comprised essentially of four parts, namely a part (2) for the posterior support and fixation of the thigh, a part (3) for the posterior support and fixation of the leg, a supporting part (4) and a part (5) for posterior support and fixation of the foot.

These four parts respectively include multiple belts, not represented in the figures, which together with parts (8) and (9) will ensure that the leg, thigh and foot lay and remain fixed against the device (1), object of this invention.

To ensure that the images obtained with the device (1) by computed axial tomography scan or magnetic resonance imaging do not show distortions, all materials used in the present invention are plastics, resins and composites.

Figure 2:
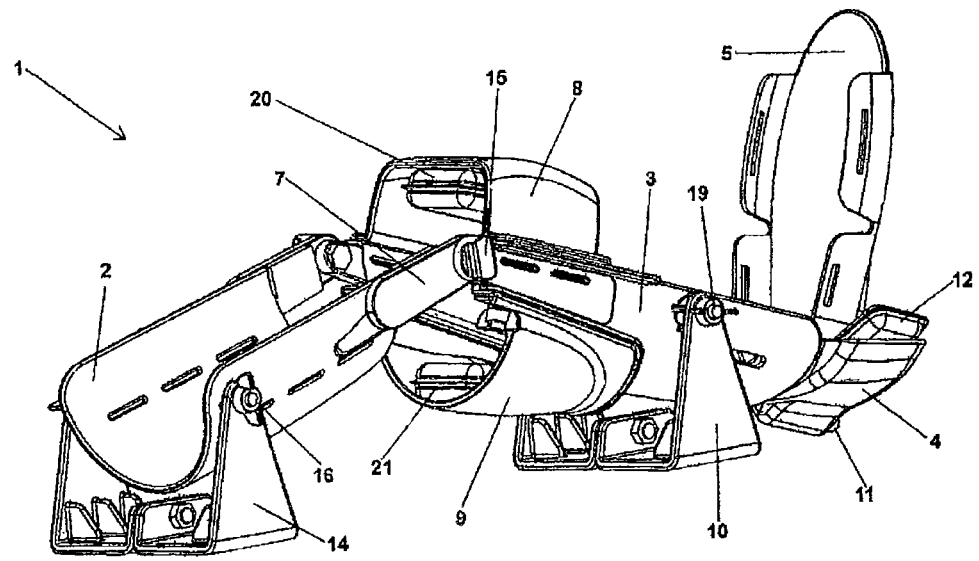

The device (1) comprises independent means (20) to push backwards the anterior zone of the leg and means (21) to push forward the posterior zone of the leg (21), shown in FIG. 2, respectively located in the inner wall of a removable part (8) for posterior support and fixation of the leg and in the inner wall of a removable part (9) for front support and fixation of the leg.

Figure 4:
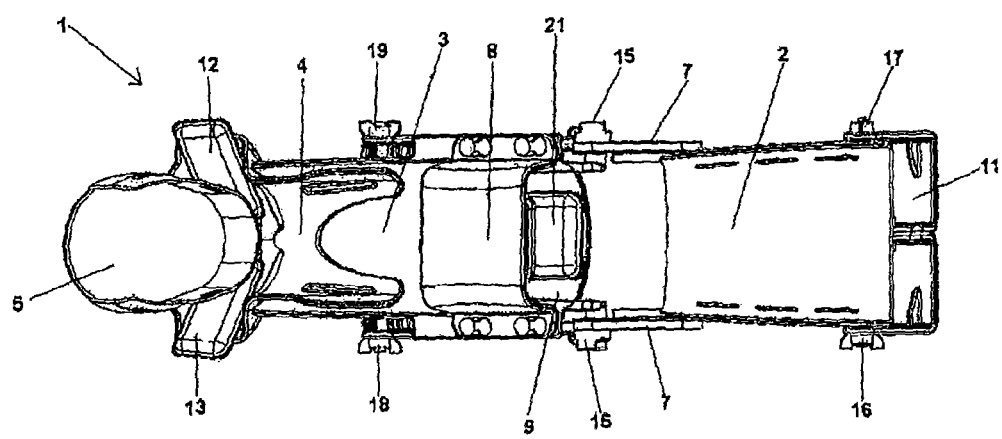
FIG. 4 is a top view of the device described in this invention.

On the other hand, in the foot zone (1), as can be seen in FIG. 4, the device also comprises means (12) to push the foot in clockwise direction, and means (13) to push the foot in anti-clockwise direction, respectively located on the inner wall on the right and left sides of a support piece (4).

These means (20), (21), (12) and (13) to push their respective leg and foot zones can be of any kind namely manually inflatable bags or compressor filled ones, or by hydraulic means.

The means (20), (21), (12) and (13) to push their respective leg and foot zones, so as to position and hold the patient foot and/or leg into position, can work independently and alternatively from each other.

Moreover, the means (20), (21) to push their respective leg zones can work in conjunction with the means (12) and (13) to push the foot, so as to position and hold the foot and/or the patient's leg into position.

Thus, as described, the present invention can position and hold the foot and/or the leg of the patient in various positions.

After applying a force on the posterior surface of the leg, or on the anterior surface of the leg, applying a force to rotate the foot internally or externally, or any one of these movements combined two by two, the device (1) will allow the measurements of translation and rotation of the knee, of the tibia over the femur, into the MRI or CAT-scan device, or any other imaging device that permits these measurements. These measurements include the evaluation in mm and/or degrees of translation and/or rotation of the tibia over the femur.

Figure 5:
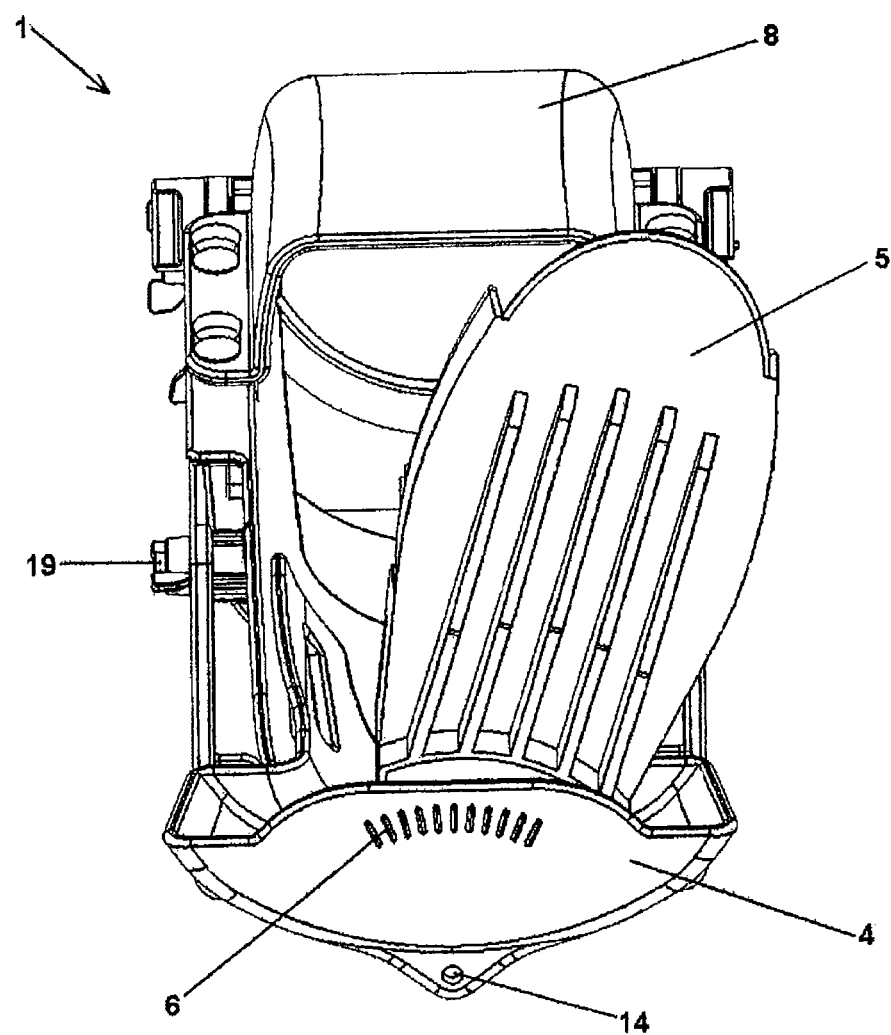
FIG. 5 is a front view of the device described in the present invention, in which one can see a scale, being the support part in an angle.

As shown in FIG. 5, the part (5) for posterior support and fixation of the foot can rotate clockwise or anticlockwise around a shaft (14), which runs through this part (5) and through a supporting part (4).

In FIGS. 1 and 5 one can also see a scale (6) located in the supporting piece (4)

In the device (1), the parts of the leg and thigh can be positioned at different angles, through the articulated elements (7) held in the desired positions by tightening nuts (15). The parts of the leg and thigh can also be adapted to various anatomical dimensions of the patient by sliding said elements (7) and parts (2, 3), and element (4), which are then fixed in the desired positions by mechanical means, not represented in the Figures, placed in openings or holes existing in those elements and parts.

Figure 3:
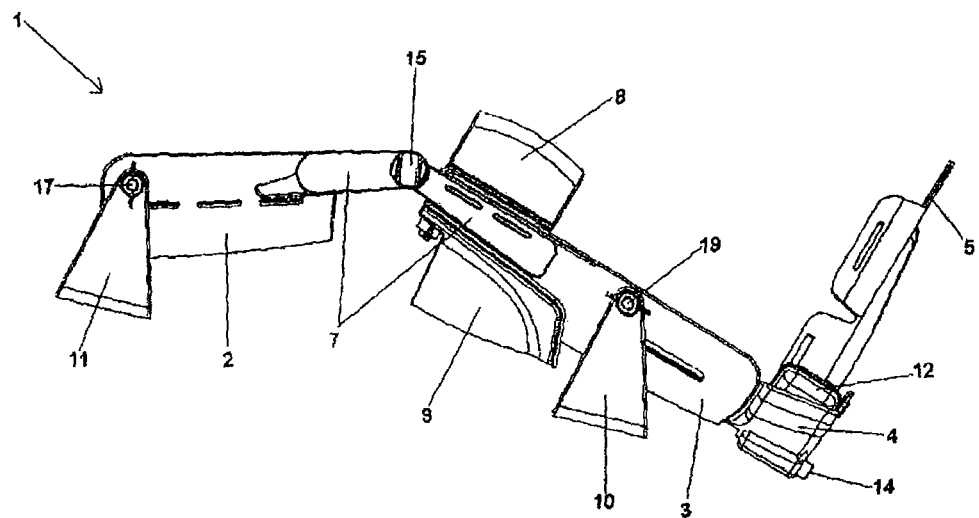
FIG. 3 is a side view of the device described in the present invention.

In FIGS. 1, 2 and 3 one can see the moving parts (10) and (11) comprising flat bases which will provide support and stability to the device (1) on a horizontal plane.

These moving parts (10) and (11) are fastened to the sides of parts (2) and (3) through tightening nuts (16-19), as shown in FIG. 4.

As it will be apparent to those skilled in the art, various detail modifications can be made, which however are considered to be included in the spirit of the invention.

The invention should be limited only by the scope of the appended claims.

The invention claimed is:

1. An apparatus for measuring knee laxity, the apparatus comprising:
    a thigh holding component for receiving and holding a thigh with belts;
    a leg holding component for receiving and holding a leg;
    a foot holding component for receiving and holding the foot with belts, the foot holding component comprising a foot fixation part adapted to support and fix the foot, and a supporting part having first and second sides comprising respective inner walls, wherein the foot fixation part is disposed in the supporting part;
    first and second pushing components for pushing backward an anterior zone of the leg and for pushing forward a posterior zone of the leg, respectively, located in an inner wall of a removable part for posterior support and fixation of the leg, and in an inner wall of a removable part for front support and fixation of the leg;
    a clockwise movement component adapted to exert a first force on the foot fixation part and cause the foot fixation part to move in a clockwise direction, the clockwise movement component being between the foot fixation part and the inner wall of the first side of the supporting part; and
    a counter-clockwise movement component adapted to exert a second force on the foot fixation part and cause the foot fixation part to move in a counter-clockwise direction, the counter-clockwise movement component being located between the foot fixation part and the inner wall of the second side of the supporting part;
    wherein the foot fixation part rotates clockwise or counter-clockwise, in response to the first or second force exerted on it, around a shaft that runs through said foot fixation part and through the supporting part which is articulated therein.

2. The apparatus of claim 1, further comprising a scale located in an outer zone of the supporting part, the scale being adapted to measure a rotation imparted to the foot.

3. The apparatus of claim 1, wherein the first and second pushing components, the clockwise movement component, and the counter-clockwise movement component function independently and alternatively from each other.

4. The apparatus of claim 1, wherein the first and second pushing components function simultaneously and in conjunction with the clockwise movement component and the counter-clockwise movement component to rotate the foot.

5. The apparatus of claim 1 wherein the clockwise movement component, the counter-clockwise movement component, and the first and second pushing components comprise inflatable elements.

6. The apparatus of claim 1, wherein the clockwise movement component, the counter-clockwise movement component, and the first and second pushing components are hydraulic.

7. The apparatus of claim 1, wherein the the leg holding component and the thigh holding component can be positioned at different angles by an articulated element fixed in a desired position by tightening nuts, and wherein the leg holding component and the thigh holding component are adaptable to various anatomical dimensions of the patient by sliding said articulated element and leg holding component and thigh holding component, and foot holding component, which are then fixed in the desired position by mechanical means placed in openings existing in those components.

8. The apparatus of claim 1, further comprising first and second moving parts with having flat bases that provide support and stability on a horizontal plane, and are attached to first and second sides of the leg holding component and the thigh holding component by tightening nuts.

9. The apparatus of claim 1, further comprising materials suitable for use in one of computed axial tomography or magnetic resonance imaging.

10. The apparatus of claim 1, wherein the inflatable elements are manually inflatable or inflatable by a compressor.

11. The apparatus of claim 10, wherein the inflatable elements are a hydraulic inflatable element, pneumatic air cylinder or an inflatable bag.

12. A process for measuring knee laxity, the process comprising using the apparatus of claim 1 to evaluate an instability of a knee due to a rupture of a ligament.

\* \* \* \* \*